(12) United States Patent
Yung

(10) Patent No.: US 7,011,950 B2
(45) Date of Patent: Mar. 14, 2006

(54) DETECTING RECURRENCE AND HIGH STAGE BLADDER CARCINOMA

(75) Inventor: Benjamin Yat Ming Yung, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 247 days.

(21) Appl. No.: 10/442,083

(22) Filed: May 21, 2003

(65) Prior Publication Data

US 2004/0248096 A1 Dec. 9, 2004

(51) Int. Cl.
*C12Q 1/68* (2006.01)

(52) U.S. Cl. .......................... 435/6; 435/7.23; 436/63; 436/64

(58) Field of Classification Search .................... 435/6, 435/7.23; 436/63, 64
See application file for complete search history.

(56) References Cited

OTHER PUBLICATIONS

Busch H The Current Status of Studies on Human Tumor Nucleolar Antigens. Cancer Res Monogr, (1987) 4 214-82.*
Chung HW Reverse transcriptase PCR (RT-PCR) and quantitative-competitive PCR ((QC-PCR) Exp Mol Med. Apr. 21, 2001;33(1 Suppl):85-97 (abstract only).*

* cited by examiner

*Primary Examiner*—Karen A. Canella
*Assistant Examiner*—Lei Yao
(74) *Attorney, Agent, or Firm*—Rosenberg, Klein & Lee

(57) ABSTRACT

Analysis of nucleophosmin/B23 mRNA expression provides sensitive, quantitative, rapid and specific analysis to detect cancer cells in tissues for predicting and monitoring recurrence and high stage bladder carcinoma. Over-expression of nucleophosmin/B23 mRNA is a useful prognostic marker for disease recurrence and high stages in bladder carcinoma. The use of such prognostic marker for the prediction of bladder tumor recurrence and high stages facilitates more effective management of the cancer.

5 Claims, 8 Drawing Sheets

| | |
|---|---|
| No. pts. | 50 |
| Mean pt. Age (range) | 67 (30-86) |
| Male/female ratio | 37/13 |
| No. T classification (%): | |
| pT1 | 35 (70) |
| pT2 | 6 (12) |
| pT3 | 8 (16) |
| pT4 | 1 (2) |
| No. histological grade (%): | |
| I | 19 (38) |
| II | 22 (44) |
| III | 9 (18) |
| No. primary tumors (%): | 34 |
| pT1 | 22 (64.7) |
| pT2 | 4 (11.8) |
| pT3 | 7 (20.6) |
| pT4 | 1 (3) |
| No. of recurrence tumors (%): | 16 |
| pT1 | 13 (81.3) |
| pT2 | 2 (12.5) |
| pT3 | 1 (6.3) |

| | $\triangle C_T < 12.5$ (n=24) | | $\triangle C_T \geq 12.5$ (n=26) | |
|---|---|---|---|---|
| | primary | recurrent | primary | recurrent |
| Stage pT1 | 3 | 10 | 19 | 3 |
| Stage pT2-pT4 | 9 | 2 | 3 | 1 |

B.

| | $\triangle C_T < 12.5$ (n=24) | | $\triangle C_T \geq 12.5$ (n=26) | |
|---|---|---|---|---|
| | primary | recurrent | primary | recurrent |
| Grade I | 2 | 7 | 10 | 0 |
| Grade II-III | 10 | 5 | 12 | 4 |

Figure 7

```
LOCUS      HUMNPM      1296 bp  ss-mRNA        PRI    26-OCT-1992
           BASE COUNT     422 a    223 c    314 g    337 t
ORIGIN
    M23613   Length: 1296  March 16, 1995 13:25  Type: N  Check: 5096 ..
       1  GGGCGGGATT CCGTCCTGCG CGGTTGTTCT CTGGAGCAGC GTTCTTTTAT
      51  CTCCGTCCGC CTTCTCTCCT ACCTAAGTGC GTGCCGCCAC CCGATGGAAG
     101  ATTCGATGGA CATGGACATG AGCCCCCTGA GGCCCCAGAA CTATCTTTTC
     151  GGTTGTGAAC TAAAGCCCGA CAAAGATTAT CACTTTAAGG TGGATAATGA
     201  TGAAAATGAG CACCAGTTAT CTTTAAGAAC GGTCAGTTTA GGGGCTGGTG
     251  CAAAGGATGA GTTGCACATT GTTGAAGCAG AGGCAATGAA TTACGAAGGC
     301  AGTCCAATTA AAGTAACACT GGCAACTTTG AAAATGTCTG TACAGCCAAC
     351  GGTTTCCCTT GGGGGCTTTG AAATAACACC ACCAGTGGTC TTAAGGTTGA
     401  AGTGTGGTTC AGGGCCAGTG CATATTAGTG GACAGCACTT AGTAGCTGTG
     451  GAGGAAGATG CAGAGTCAGA AGATGAAGAG GAGGAGGATG TGAAACTCTT
     501  AAGTATATCT GGAAAGCGGT CTGCCCCTGG AGGTGGTAGC AAGGTTCCAC
     551  AGAAAAAAGT AAAACTTGCT GCTGATGAAG ATGATGACGA TGATGATGAA
     601  GAGGATGATG ATGAAGATGA TGATGATGAT GATTTTGATG ATGAGGAAGC
     651  TGAAGAAAAA GCGCCAGTGA AGAAATCTAT ACGAGATACT CCAGCCAAAA
     701  ATGCACAAAA GTCAAATCAG AATGGAAAAG ACTCAAAACC ATCATCAACA
     751  CCAAGATCAA AAGGACAAGA ATCCTTCAAG AAACAGGAAA AAACTCCTAA
     801  AACACCAAAA GGACCTAGTT CTGTAGAAGA CATTAAAGCA AAAATGCAAG
     851  CAAGTATAGA AAAAGGTGGT TCTCTTCCCA AAGTGGAAGC CAAATTCATC
     901  AATTATGTGA AGAATTGCTT CCGGATGACT GACCAAGAGG CTATTCAAGA
     951  TCTCTGGCAG TGGAGGAAGT CTCTTTAAGA AAATAGTTTA AACAATTTGT
    1001  TAAAAAATTT TCCGTCTTAT TTCATTTCTG TAACAGTTGA TATCTGGCTG
    1051  TCCTTTTTAT AATGCAGAGT GAGAACTTTC CCTACCGTGT TTGATAAATG
    1101  TTGTCCAGGT TCTATTGCCA AGAATGTGTT GTCCAAAATG CCTGTTTAGT
    1151  TTTTAAAGAT GGAACTCCAC CCTTTGCTTG GTTTTAAGTA TGTATGGAAT
    1201  GTTATGATAG GACATAGTAG TAGCGGTGGT CAGACATGGA AATGGTGGGG
    1251  AGACAAAAAT ATACATGTGA AATAAAACTC AGTATTTTAA TAAAGT
Primer : F-5' C C A G T G G T C T T A A G G  T T G A A G T G T G G -3'
        :R-5' G G A G G A G G A T G T G A A A C T C T T A A G T A T A T C T G G A -3'
Probe : T C A G G G C C A G T G C A T A T T A G T G G A C A G C A C T T A G T A G C T
```

Using in the experiment

Sequence name : B23 RIMER-F

Length: 26 mers

Sequence : 5'→3'

CCA GTG GTC TTA AGG TTG AAG TGT GG

Sequence name: B23 primer-R

Length: 34 mers

Sequence : 5'→3'

TCC AGA TAT ACT TAA GAG TTT CAC ATC CTC CTC C

Sequence name : B23 PROBE

Length: 39 mers

6-FAM- AGC TAC TAA GTG CTG TCC ACT AAT ATG CAC TGG CCC TGA -TAMRA

Figure 8

SEQUENCE LISTING

<160> NUMBER OF SEQ ID NOS: 3

<210> SEQ ID NO 1
<211> LENGTH: 26
<212> TYPE: DNA
<213> ORGANISM: Homo sapiens

<400> SEQUENCE: 1
ccagtggtct taaggttgaa gtgtgg                                    26

<210> SEQ ID NO 2
<211> LENGTH: 33
<212> TYPE: DNA
<213> ORGANISM: Homo sapiens

<400> SEQUENCE: 2
tccagatata cttaagagtt tcacatcctc ctc                            33

<210> SEQ ID NO 3
<211> LENGTH: 39
<212> TYPE: DNA
<213> ORGANISM: Homo sapiens

<400> SEQUENCE: 3
agctactaag tgctgtccac taatatgcac tggccctga                      39

DETECTING RECURRENCE AND HIGH STAGE BLADDER CARCINOMA

BACKGROUND OF THE INVENTION

1. Field of the Invention

The present invention relates to cancer diagnosis. More specifically, the present invention discloses methods for diagnosing disease recurrence and high stage bladder carcinoma.

2. Description of the Prior Art

Many superficial tumors recur, of which some progress to become muscle invasive cancer. The treatment of bladder transitional cell carcinoma is dictated by several factors. The most clinically significant prognostic parameters for tumor recurrence and invasion of bladder cancer are grade, stage, lymphatic invasion, tumor size, carcinoma in situ, multifocality and the rate of tumor recurrence. Of these parameters, pathological stage and tumor grade are seen as most important. However, staging errors are possible. Under-staging occurs in cases of high and intermediate stage disease, of which approximately 33% are typically under-staged and 10% are typically over-staged, respectively. An ideal prognostic factor must be reliable to direct treatment decisions in individuals.

Cytologic analysis of voided urine is the most commonly used non-invasive method for detecting transitional cell carcinoma, but its utility is severely constrained by its low sensitivity.

Several potential diagnostic markers for bladder cancer have been identified, including nuclear matrix protein 22, bladder tumor antigen, and telomerase. Although these markers are more sensitive than urine cytology for detecting bladder cancer, their use is limited by low specificity. Specific genetic alterations have been implicated in the molecular pathogenesis of transitional cell carcinoma, with mutations reported in cell cycle regulatory genes, oncogenes, and tumor suppressor genes. However, it has proven difficult to use these genetic alterations as diagnostic markers of bladder cancer because of their low sensitivity.

Therefore, there is a need for a more efficient and effective method for diagnosing disease recurrence and high stage bladder carcinoma.

SUMMARY OF THE INVENTION

To achieve these and other advantages and in order to overcome the disadvantages of conventional methods in accordance with the purpose of the invention as embodied and broadly described herein, the present invention provides a method for diagnosing disease recurrence and high stage bladder carcinoma.

As noted above, staging errors are possible during diagnosis. Under-staging occurs in cases of high and intermediate stage disease, of which approximately 33% are under-staged and 10% are over-staged, respectively. An ideal prognostic factor must be reliable to direct treatment decisions in individuals.

Additionally, the utility of cytologic analysis of voided urine is severely constrained by its low sensitivity.

Furthermore, several potential diagnostic markers for bladder cancer have been identified but their use is limited by low specificity. Additionally, it has proven difficult to use these genetic alterations as diagnostic markers of bladder cancer because of their low sensitivity.

Therefore, there is a need for a more efficient and effective method for diagnosing disease recurrence and high stage bladder carcinoma.

The role of nucleophosmin/B23 in control of cancer growth has been studied, but until now, little is known about nucleophosmin/B23 expression status in cancer tissues. The results of mRNA expression status of nucleophosmin/B23 gene using RT-PCR indicate that over-expression of nucleophosmin/B23 is important for the tumorigenesis of bladder cancer. In a study of patients with bladder carcinoma, it was found that in pT1 cases, 22 (62.9%) of 35 patients had low expression of nucleophosmin/B23 ($\Delta Ct \geq 12.5$). In contrast, 11 (73.3%) of 15 patients of in pT2–T4 had high expression of nucleophosmin/B23 ($\Delta Ct < 12.5$). Furthermore, 22 (64.7%) of 34 patients of primary cancer had low expression of nucleophosmin/B23 ($\Delta Ct \geq 12.5$) while 12 (75.0%) of 16 patients of recurrent cancer had high expression of nucleophosmin/B23 ($\Delta Ct < 12.5$).

Significant links exist between nucleophosmin/B23 over-expression with high tumor stage and with tumor recurrence. Nucleophosmin/B23 gene may thus be associated with an increased risk of high stage and recurrence. Moreover, it is important to note that 10 (76.9%) of 13 cases of pT1 stage or 7 (77.8%) of 9 cases of tumor grade I, having over-expression of the nucleophosmin/B23 ($\Delta Ct < 12.5$) are recurrent tumors. In analysis of those nucleopohosmin/B23 over-expressed tumors, the majority of them were either recurrent or at high stages. Therefore, there is high probability that tumors having over-expression of nucleophosmin/B23 ($\Delta Ct < 12.5$) will recur or become tumors of high stages. The results imply that patients with tumors over-expressing nucleophosmin/B23 would relapse more frequently and have significantly shorter relapse-free survival after surgery compared with patients whose tumors having low expression of nucleophosmin/B23.

Down-regulation of nucleophosmin/B23 may be predictive of recurrence-free survival while nucleophosmin/B23 over-expression is associated with a poor prognosis. The nucleophosmin/B23 expression status is therefore useful as a molecular marker for the prediction of tumor recurrence and high stage. The utilization of such useful prognostic marker for the prediction of bladder tumor recurrence and high stage facilitates more effective management of this cancer.

One important difference between cancer and normal cells is hyperactivity and pleomorphism of the nucleoli. The nucleolus in cancer cells undergoes extreme variations in size, shape, fine structure, and cytochemical composition. Uncontrolled cell proliferation is the hallmark of cancer, and tumor cells have typically acquired damage to genes that directly regulate their cell cycles and cell growth. Although rRNA transcription, processing and ribosome assembly have been established as major functions of nucleolus, previous studies suggest that nucleolus participates in many other aspects of gene expression as well. New results indicate that biosyntheses of signal recognition particle RNA and telomerase RNA involve a nucleolar stage and nucleolus is a site critical to cellular aging.

A number of studies indicate that nucleophosmin/B23, one of the major nucleolar phosphoproteins, plays a role in increased nucleolar activity that is necessary for cell proliferation. Down-regulation of nucleophosmin/B23 is associated with two different growth control pathways, cellular differentiation and apoptosis. Nucleophosmin/B23 is transcriptionally down-regulated during induction of cellular differentiation and apoptosis. Nucleophosmin/B23 antisense oligomer treatment significantly potentiates induction of cellular differentiation, apoptosis and inhibition of telomerase activity. In support of the idea that down-regulation of nucleophosmin/B23 plays a role in cell proliferation, the steady-state level of nucleophosmin/B23 mRNA is significantly higher in abnormal growth than in normal growth. Nucleophosmin/B23 is importantly associated with cancer.

The other important findings about nucleophosmin/B23 related to these studies are that nucleophosmin/B23 synthesis decreases during apoptosis in Jurkat T-lymphoblasts, and that nucleophosmin/B23 may play a downstream role in the apoptotic cascade. The potentiation ability of nucleophosmin/B23 antisense in induced cellular differentiation and apoptosis is particularly interesting and may lead to the use of antisense construct in cancer treatment. In any case, nucleophosmin/B23 gene is implicated to have a functional role in growth control, and its expression has a causal relationship with susceptibility of tumor cells to induced differentiation and apoptosis. Nucleophosmin/B23 could thus be an important anti-cancer target.

The present invention indicates the involvement of nucleophosmin/B23 in bladder tumorigenesis. Treatment strategies can be determined based on nucleophosmin/B23 expression used as part of evidence-based medical treatment. Nucleophosmin/B23 over-expression which frequently occurs in recurrent and high-staged bladder cancers is a strong indicator of invasive stage and high recurrence rate in cases of bladder carcinoma. Nucleophosmin/B23 over-expression can be used with TNM system and serve as a useful, specific tool to provide crucial information about the treatment and prognosis.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings, FIG. 1 is a table showing characteristics of patients with bladder carcinoma;

FIG. 7 is a chart illustrating a summary of the number of tumors having high or low expression of nucleophosmin/B23 mRNA at various stages and grades; and FIG. 8 is a Nucleophosmin/B23 mRNA sequence listing.

DESCRIPTION OF THE PREFERRED EMBODIMENTS

Figure 2:
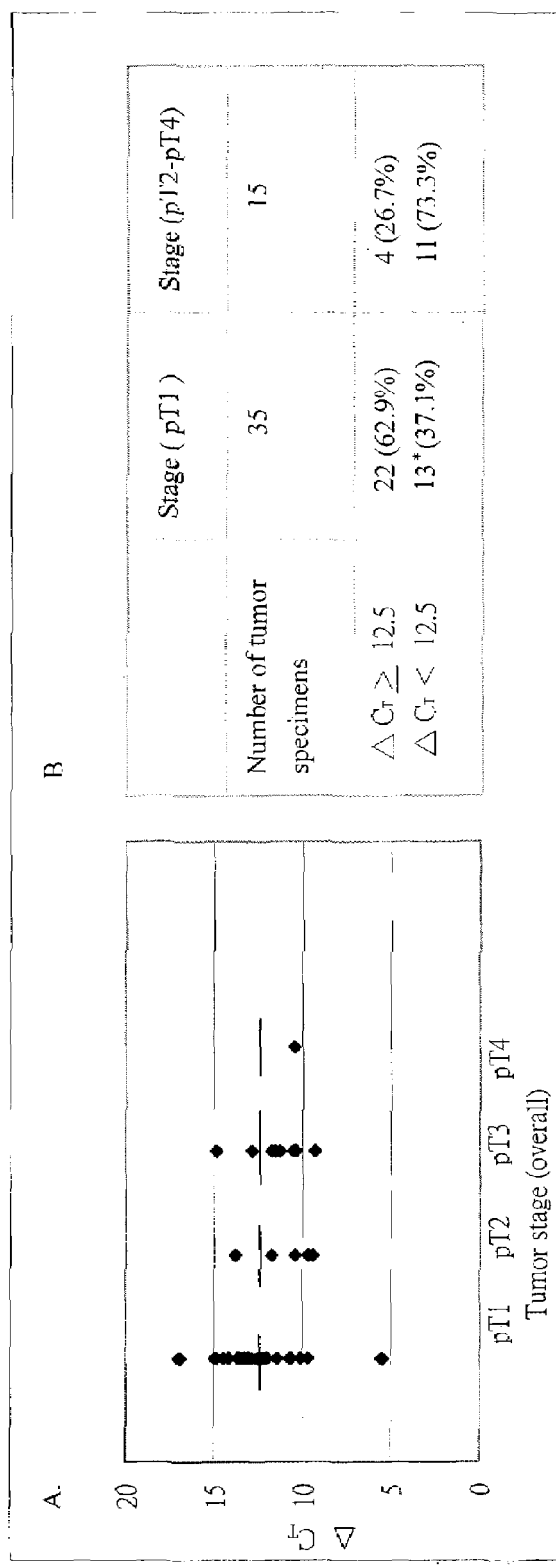
FIG. 2 is a graph illustrating nucleophosmin/B23 mRNA levels and tumor stages.

Reference will now be made in detail to the preferred embodiments of the present invention, examples of which are illustrated in the accompanying drawings. Wherever possible, the same reference numbers are used in the drawings and the description to refer to the same or like parts.

The present invention discloses the involvement of nucleophosmin/B23 in bladder tumorigenesis. Treatment strategies can be determined based on nucleophosmin/B23 expression used as part of evidence-based medical treatment. Nucleophosmin/B23 over-expression which frequently occurs in recurrent and high-staged bladder cancers is a strong indicator of invasive stage and high recurrence rate in cases of bladder carcinoma. Nucleophosmin/B23 over-expression can be used with TNM system and serve as a useful, specific tool to provide crucial information about the treatment and prognosis.

In implementation, after a patient is diagnosed with bladder cancer, surgery is performed to remove the tumor. The tumor is then hispathologically examined using a Tumor, Nodes, Metastasis (TNM) system to determine grading and staging. The tumor stage is designate by a T value of from one to four. An alphabetic subcategory adds further classification, for example, T3a. Early stage tumors include stages T1 and T2.

The grade of a cancer is a representation of how fast the tumor cells are growing. Grades can range from two to ten. The larger the grade designates the probability that the tumor cells will grow quickly and spread to other areas.

Next real-time reverse transcription polymerase chain reaction is performed to measure the Nucleophosmin/B23 mRNA expression. After the Nucleophosmin/B23 mRNA expression is measured the ΔCt value is determined. The ΔCt is the difference in the Ct values derived from the Nucleophosmin/B23 gene being assayed and the 18S control. After the ΔCt value is determined it is compared to the ΔCt of MGH-U4 cells which is 12.5. If the ΔCt of the patient's sample is less than 12.5 it is considered to be having over-expression of Nucleophosmin/B23 and is very likely to recur or become a high stage tumor. As a result of using this method, more effective management of the cancer can be achieved.

For an example, the following case study is presented. Fifty patients took part in the study.

Refer to FIG. 1, which is a table showing characteristics of patients with bladder carcinoma.

Tumor samples from a total of 50 patients with histopathologically confirmed bladder transitional cell carcinoma and early-staged MGH-UH bladder cancer cells were analyzed. All assays were performed using RT-PCR which yielded a value (Ct) denoting the threshold cycle of PCR amplification at which product was first detected by fluorescence. ΔCt was the difference in the Ct values derived from the nucleophosmin/B23 gene being assayed and the 18S ribosomal RNA control. The ΔCt value for MGH-U4 was about 12.5 that was assigned to be the cutoff threshold. Samples with ΔCt values less than 12.5 wee considered to be having over-expression of nucleophosmin/B23 or vise versa.

The population included 37 men and 13 women of 30 to 86 years old (mean age 67). Patients followed postoperatively for a median of 10 months. The eligibility criteria included the following: (1) complete transurethral resection (TUR) of all visible tumors, biopsy of the underlying muscle, and selected cold-cup biopsies of suspected mucosal areas, (2) pathologically proven transitional cell carcinoma of the bladder. The exclusion criteria included previous exposure to radiotherapy or chemotherapy, a history of other active malignancy, unavailability for periodic follow-up, and any other reason for exclusion on the basis of the judgment of the attending physician.

Cases of transitional cell carcinoma were staged and graded pathologically according to the International Union against Cancer TNM and WHO classifications after transurethral resection for superficial tumor and total cystectomy for invasive tumor. Preoperative performance status was determined for all patients according to the Eastern Cooperative Oncology Group (ECOG) scale as 0: normal activity, 1: symptomatic but ambulatory, 2: bedridden less than 50% of the time, 3: bedridden more than 50% of the time, and 4: completely bedridden.

A MGH-U4 cell line derived from a male who had a bladder tumor of carcinoma in situ and severe atypia of the bladder was used as a control. MGH-U4 cells were grown in RPMI 1640 medium supplemented with 10% fetal bovine serum and 1% antibiotics in 5% CO2 humidified incubator at 37 degrees C.

Approximately 20 mg of tissue was obtained from each sample for RNA extraction using TRIzol reagent. The purification procedure was performed according to the manufacture's protocol. The quality of RNA samples was determined by electrophoresis on agarose gel and by visualization of the integrity of the 18S and 28S RNA bands. The concentration, purity, and amount of total RNA were determined by ultraviolet spectrophotometry. By these standards, all the RNA samples used for assay were of high quality and purity (Abs 260/Abs280>1.7). The reverse transcription reaction was performed by incubating a reaction mixture containing 300 ng total RNA, 6 $\mu$l of 5× First buffer [250 mM Tris-HCL (pH8.3), 375 mM KCL, 15 mM MgCl2], 20 $\mu$M of random haxamer primer, 50 U of reverse transcriptase, 10 U of RNase inhibitor, and 0.5 mM dNTP in a total of 30 $\mu$l reaction buffer at 42 degrees C. for 1 hour.

Primers and probes for each gene were chosen. For each primer and probe, we conducted a BLASTN search against the GenBank database to confirm the total gene specificity and the absence of DNA polymorphism. The PCR amplicon regions for nucleophosmin/B23 contained all the possible splicing products to ensure the measurement of total mRNA expression. The primers and probes used for RT-PCR are B23 primer-Forward (5'-CCAGTGGTCTTAAGGT-TGAAGTGTGG-3'), B23 primer-Reverse (5'-TCCA-GATATACTTAAGAGTTTCACATCCTCCTC-3') and B23 probe (5'-AGCTACTAAGTGCTGTCCACTAATATG-CACTGGCCCTGA-3'). They were labeled with FAM as the reporter. All PCR reactions were performed using an ABI Prism 5700 Sequence Detection System. For each PCR run, a master mix was prepared on ice with TaqMan Universal PCR Master Mix, 400 mM primer, 200 mM probe and 3 $\mu$l of cDNA in a total of 25 $\mu$l solution. The thermal cycling conditions were an initial denaturation step at 95 degrees C. for 10 minutes, 40 cycles at 95 degrees C. for 15 seconds, and 60 degrees C. for 1 minute.

Results of the RT-PCR data were represented as Ct values, where Ct was defined as the threshold cycle of PCR at which amplified product was first detected. For the RNA internal control, we derived a Ct using 18S ribosome mRNA expression. The PCR reaction and protocol for the 18S ribosome were the same as described above. ΔCt was the difference in the Ct values derived from the specific gene being assayed and the 18S control.

To examine the relative expression of the nucleophosmin/B23 mRNA, the ΔCt values from tumor tissues were compared with that of MGH-U4 cells. The correlation between pathological stages and ΔCt values of RT-PCR were determined.

Of the 50 patients who underwent tumor excision surgery, there were 35 patients (70%) with stage T1, 6 patients (12%) with stage T2, 8 patients (16%) with stage T3 and 1 patient (2%) with stage T4. Nineteen (38%) of 50 cases were Grade I, 22 (44%) were Grade II and 9 (18%) were Grade III. Preoperative performance status determined for all patients according to the Eastern Cooperative Oncology Group (ECOG) status was 1 to 2. Analysis revealed that 34 (68%) of 50 lesions were primary and 16 (32%) were recurrent tumors. Twenty-two (64.7%) of 34 primary tumors were pT1, 4 (11.8%) were pT2, 7 (20.6%) were pT3 and 1 (2.9%) was pT4. Thirteen (81.3%) of 16 recurrent tumors were pT1 stage, 2 (12.5%) were pT2 stage and 1 (6.3%) was pT3 stage.

Real-time reverse transcription polymerase chain reaction (RT-PCR) was performed on MGH-U4 cell line derived from a male who had a bladder tumor of carcinoma in situ and severe atypia of the bladder. A value (Ct) denotes the threshold cycle of PCR amplification at which mRNA product was first detected by fluorescence. ΔCt is the difference in the Ct values derived from the nucleophosmin/B23 gene being assayed and the 18S rRNA control. The ΔCt value for such early-staged MGH-U4 cells was found to be 12.5±0.77. ΔCt 12.5 was assigned to be the cutoff threshold. Samples with ΔCt values less than 12.5 were considered to be having over-expression of nucleophosmin/B23 as compared with MGH-U4 cells and visa versa.

Figure 3:
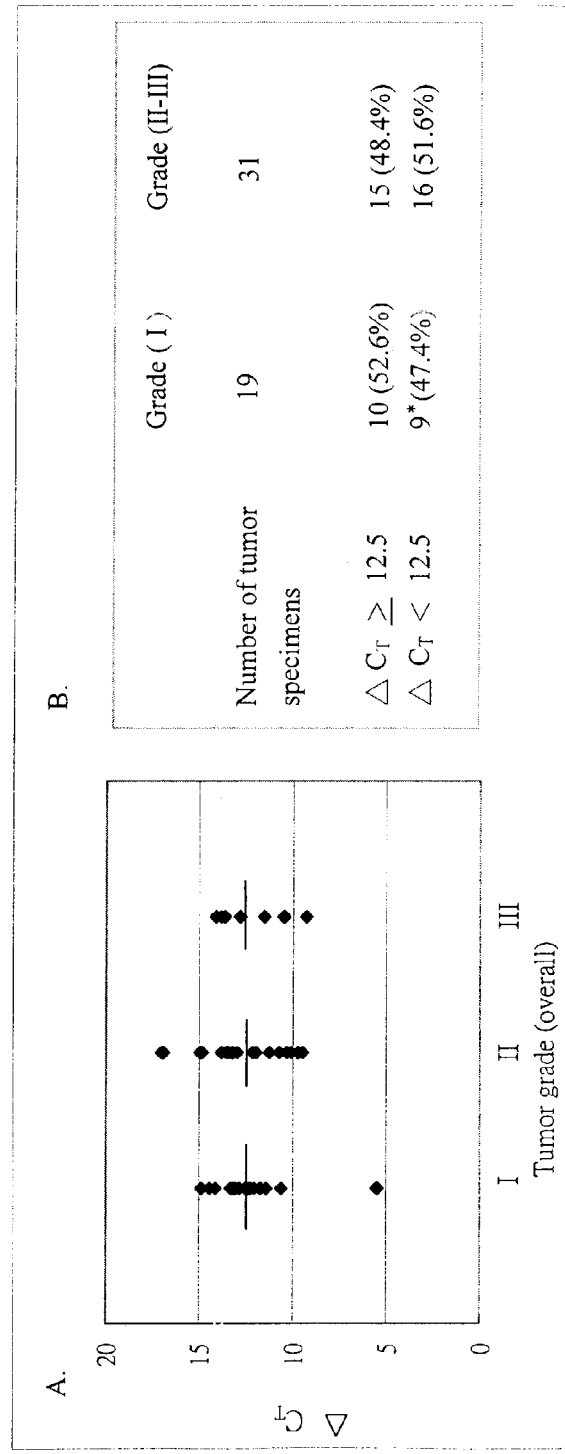
FIG. 3 is a graph illustrating nucleophosmin/B23 mRNA levels and tumor grades.

Refer to FIG. 2, which is a graph illustrating nucleophosmin/B23 mRNA levels and tumor stages and FIG. 3, which is a graph illustrating nucleophosmin/B23 mRNA levels and tumor grades.

In FIGS. 2 and 3, the horizontal bars indicate the ΔCt cutoff value of 12.5. In FIG. 2, a high percentage (62.9%) of pT1 samples had ΔCt≧12.5, while a high percentage (73.3%) of pT2–T4 samples had ΔCt<12.5. Ten of 13 tumors of pT1 stage having ΔCt<12.5 were recurrent diseases.

In FIG. 3, 52.6% of grade (I) samples had ΔCt≧12.5, while 47.4% of grade (II–III) samples had ΔCt<12.5. Seven of nine tumors of Grade (I) having ΔCt<12.5 were recurrent diseases.

Analysis of the correlation between Nucleophosmin/B23 mRNA expression with T classification and tumor grade was examined for possible association of nucleophosmin/B23 mRNA status with standard clinical and pathological factors in bladder cancer. Twenty-two (62.9%) of 35 pT1 cases had ΔCt≧12.5 (ranged 12.6 to 17.0). In contrast, 11 (73.3%) of 15 pT2–T4 cases had ΔCt<12.5 (ranged 5.4 to 12.4). Over-expression of nucleophosmin/B23 (ΔCt<12.5) was thus detected in a majority of tumors of high stages (pT2–T4). A significant relationship was found between nucleophosmin/B23 mRNA expression and tumor stage (p<0.001). Furthermore, 10 (52.6%) of 19 cases of Grade I had ΔCt≧12.5 while 9 (47.4%) had ΔCt<12.5. Similarly, 15 (48.4%) or 16 (51.6%) of 31 Grade II–III tumors had ΔCt≧12.5 or ΔCt<12.5, respectively. No significant relationship was found between nucleophosmin/B23 mRNA expression and tumor grade (p=2.855).

Figure 4:
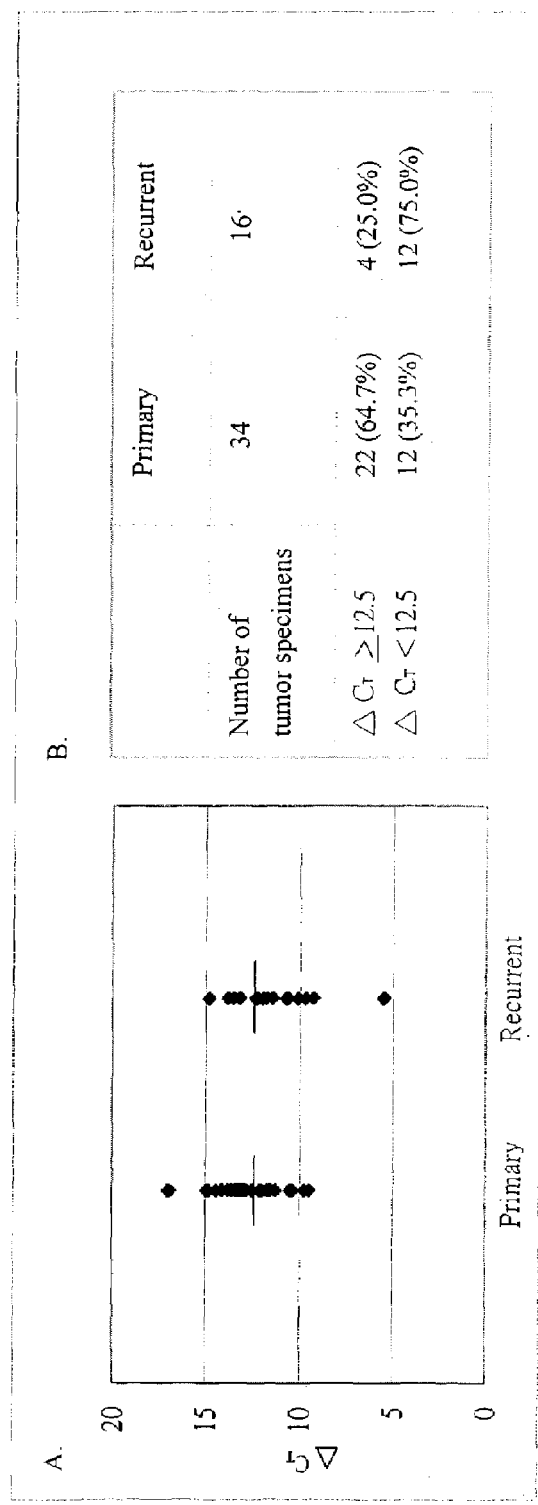
FIG. 4 is a graph illustrating nucleophosmin/B23 mRNA levels in primary and recurrent tumors.

Refer to FIG. 4, which is a graph illustrating nucleophosmin/B23 mRNA levels in primary and recurrent tumors.

In FIG. 4, the horizontal bars indicate the ΔCt cutoff value of 12.5. In FIG. 4, a high percentage (64.7%) of primary tumor samples had ΔCt≧12.5, while a high percentage (75%) of recurrent tumors had ΔCt<12.5.

Analysis of the correlation between nucleophosmin/B23 mRNA expression and tumor recurrence was performed to analyze the possible relationship between nucleophosmin/B23 mRNA expression and tumor recurrence. Twenty-two (64.7%) of 34 primary tumors had $\Delta Ct \geq 12.5$. Importantly, high expression of nucleophosmin/B23 ($\Delta Ct<12.5$) was detected in 12 (75.0%) of 16 recurrent tumors. Furthermore, it was also noted that 10 (76.9%) of 13 pT1 and 7 (77.8%) of 9 grade I tumors having high expression of nucleophosmin/B23 ($\Delta Ct<12.5$) were recurrent tumors. The results indicated that there might be a significant link between nucleophosmin/B23 mRNA over-expression and tumor recurrence.

Figure 5:
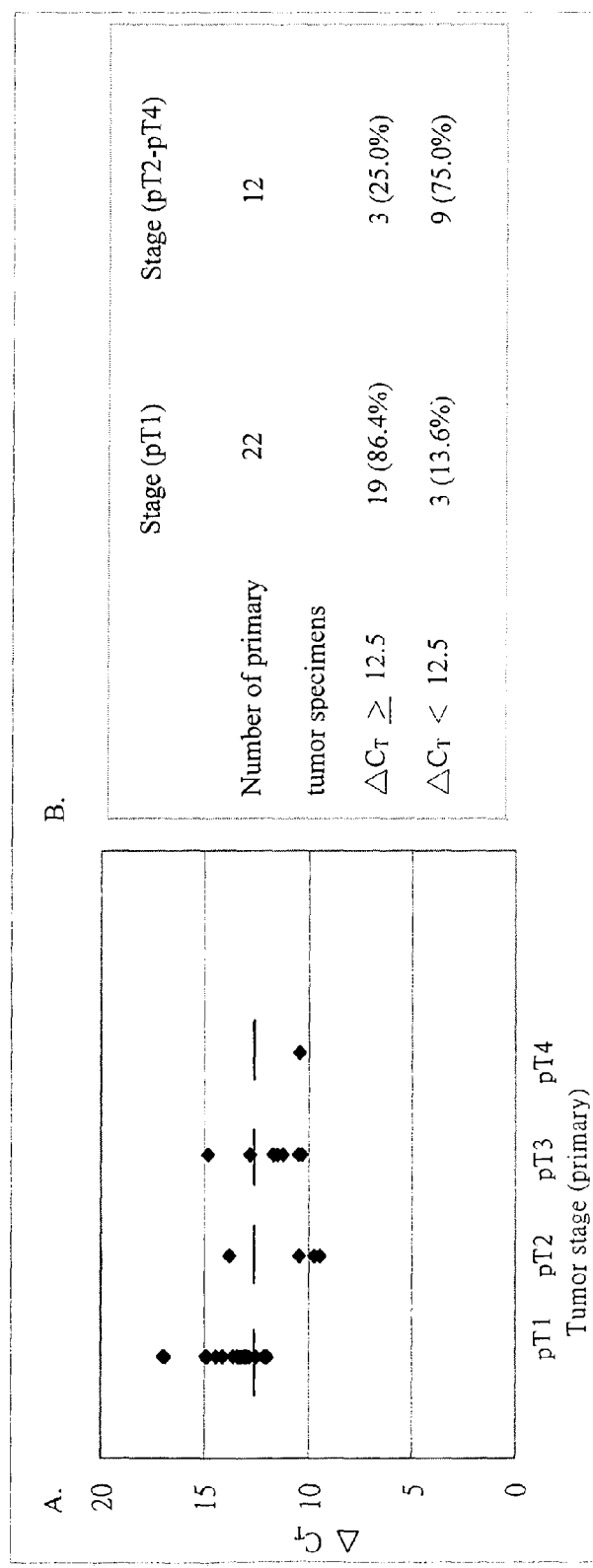
FIG. 5 is a graph illustrating nucleophosmin/B23 mRNA levels in primary tumors of various stages.
Figure 6:
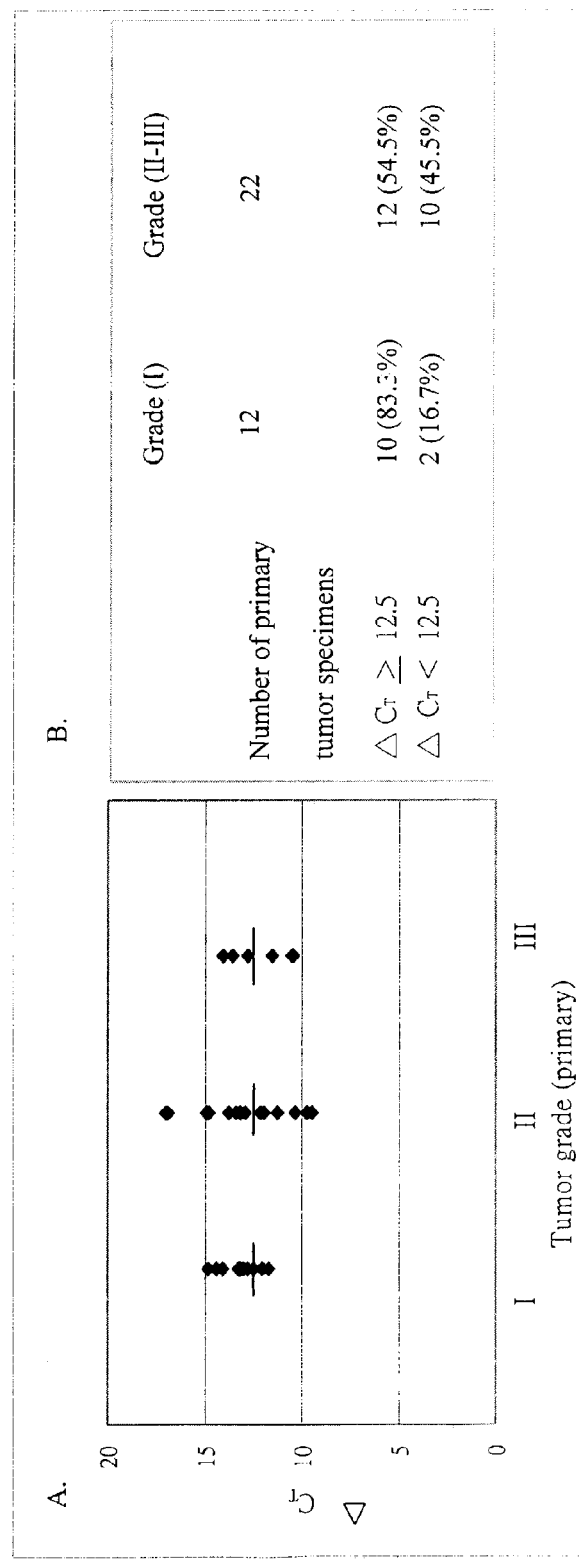
FIG. 6 is a graph illustrating nucleophosmin/B23 mRNA levels in primary tumors of various grades.

Refer to FIG. 5, which is a graph illustrating nucleophosmin/B23 mRNA levels in primary tumors of various stages and FIG. 6, which is a graph illustrating nucleophosmin/B23 mRNA levels in primary tumors of various grades.

In FIGS. 5 and 6, the horizontal bars indicate the $\Delta Ct$ cutoff value of 12.5. In FIG. 5, a high percentage (86.4%) of primary tumors of pT1 stage had $\Delta Ct \geq 12.5$, while a high percentage (75%) of primary tumors of pT2–T4 had $\Delta Ct<12.5$.

In FIG. 6, a high percentage (83.3%) of primary tumors of grade (I) stage had $\Delta Ct \geq 12.5$, while about 45.5% of primary tumors of grade (II–III) had $\Delta Ct<12.5$.

The correlation between Nucleophosmin/B23 mRNA expression with tumor stage and grade in primary tumors was analyzed. Of the 34 patients with primary tumors, 22 were stage pT1 while 12 were pT2–T4. Nineteen (86.4%) of 22 pT1 primary tumors had $\Delta Ct \geq 12.5$. High expression of nucleophosmin/B23 ($\Delta Ct<12.5$) was detected in 9 (75.0%) of 12 pT2–T4 primary tumors. Furthermore, histological analysis revealed that 12 of 34 primary tumors were Grade I, and 22 were Grade II–III. Low expression of nucleophosmin/B23 ($\Delta Ct \geq 12.5$) was detected in a majority (83.3%; 10 of 12) of Grade I primary tumors. There were 12 (54.5) or 10 (45.5%) of 22 Grade II–III primary tumors having high $\Delta Ct$ ($\geq 12.5$) or low $\Delta Ct$ (<12.5), respectively. Moreover, it was important to note that 9 (75.0%) or 10 (83.3%) of 12 primary nucleophosmin/B23 over-expressed tumors ($\Delta Ct<12.5$) were at high stages (pT2–T4) or high grades (II–III), respectively.

Refer to FIG. 7, which is a chart illustrating a summary of the number of tumors having high or low expression of nucleophosmin/B23 mRNA at various stages and grades.

FIG. 7 summarizes the number of tumors having high ($\Delta Ct<12.5$) or low ($\Delta Ct \geq 12.5$) expression of nucleophosmin/B23 at various stages and grades. It was noted that only 3 (12.5%) of 24 nucleophosmin/B23 over-expressed tumors ($\Delta Ct<12.5$) were primary and at early stage pT1 while the majority (21 of 24, 87.5%) of tumors were either recurrent or at high stages (pT2–T4). Similarly, only 2 (8%) of 24 nucleophosmin/B23 over-expressed tumors ($\Delta Ct<12.5$) were primary and at low grade (I) while the other 22 (92.0%) were either recurrent or at high grades (II–III). The results demonstrate that tumors having over-expression of nucleophosmin/B23 ($\Delta Ct<12.5$) will recur or become tumors of high stages or grades.

Refer to FIG. 8, which is a Nucleophosmin/B23 mRNA sequence listing.

It will be apparent to those skilled in the art that various modifications and variations can be made to the present invention without departing from the scope or spirit of the invention. In view of the foregoing, it is intended that the present invention cover modifications and variations of this invention provided they fall within the scope of the invention and its equivalent.

A sequence listing for the B23 primer-Forward, the B23 primer-Reverse and the B23 probe are attached as an Appendix to this Application as both a paper copy and a copy in computer readable form (CRF), in accordance with U.S. Patent and Trademark Office Rules and Regulations.

What is claimed is:

1. A method for detecting disease recurrence and high stage in bladder carcinoma comprising utilizing Nucleophosmin/B23 messenger ribonucleic acid (mRNA) as a diagnostic marker to detect disease recurrence and high stage progression of the carcinoma.

2. A method for detecting disease recurrence and high stage in bladder carcinoma comprising the steps of:
   performing real-time reverse transcription polymerase chain reaction (RT-PCR) on a tumor to measure Nucleophosmin/B23 messenger ribonucleic acid (mRNA) to obtain a Ct value, whereby the Ct value denotes a threshold cycle of PCR amplification at which a PCR product was first detected by fluorescence; and
   determining a difference value ($\Delta$Ct) between the Ct value and a control value, whereby the control value is derived from an 18S internal control.

3. The method of claim 2, whereby if the difference value is less than 12.5, the tumor has over-expression of Nucleophosmin/B23 and will recur or become a high stage tumor.

4. A method for detecting disease recurrence and high stage in bladder carcinoma comprising the steps of:
   performing real-time reverse transcription polymerase chain reaction (RT-PCR) on a tumor to measure Nucleophosmin/B23 messenger ribonucleic acid (mRNA) to obtain a Ct value;
      whereby said Ct value denotes a threshold cycle of PCR amplification at which a PCR product was first detected by fluorescence; and
   determining a difference value ($\Delta$Ct) between said Ct value and a control value;
      whereby said control value is derived from an 18S internal control; and
      whereby, if said difference value is less than a set 12.5, the tumor has over-expression of Nucleophosmin/B23 and will recur or become a high stage tumor.

5. A method for predicting disease recurrence and high stage in bladder carcinoma comprising the steps of:
   diagnosing a patient with a cancer tumor;
   performing surgery to remove the cancer tumor;
   performing hispathological examination using a Tumor, Nodes, Metastasis (TNM) system to determine grading and staging of the tumor;
   performing real-time reverse transcription polymerase chain reaction (RT-PCR) on the tumor to measure Nucleophosmin/B23 messenger ribonucleic acid (mRNA) to obtain a Ct value;
      whereby said Ct value denotes a threshold cycle of PCR amplification at which a PCR product was first detected by fluorescence; and
   determining a difference value ($\Delta$Ct) between said Ct value and a control value;
      whereby said control value is derived from an 18S internal control; and
      whereby, if said difference value is less than 12.5, the tumor has over-expression of Nucleophosmin/B23 and will recur or become a high stage tumor.

* * * * *